US 6,712,017 B2

(12) United States Patent
Harrie et al.

(10) Patent No.: US 6,712,017 B2
(45) Date of Patent: Mar. 30, 2004

(54) METHOD AND ARRANGEMENT RELATING TO INSPECTION

(75) Inventors: Per Harrie, Hovas (SE); Johan Fagerhom, Billdal (SE); Michael Kurdve, Vejbystrand (SE); Johan Lindsjo, Skivarp (SE)

(73) Assignee: Tapiren Survey System AB (SE)

( * ) Notice: Subject to any disclaimer, the term of this patent is extended or adjusted under 35 U.S.C. 154(b) by 0 days.

(21) Appl. No.: 10/303,380

(22) Filed: Nov. 22, 2002

(65) Prior Publication Data

US 2003/0106480 A1 Jun. 12, 2003

Related U.S. Application Data

(63) Continuation of application No. PCT/SE01/01182, filed on May 25, 2001.
(60) Provisional application No. 60/207,133, filed on May 24, 2000.

(30) Foreign Application Priority Data

May 24, 2000 (SE) ................................................ 0001970

(51) Int. Cl.⁷ .................................................. B63B 9/00
(52) U.S. Cl. .................................................... 114/221 R
(58) Field of Search ............................ 114/222, 221 R, 114/312

(56) References Cited

U.S. PATENT DOCUMENTS

| 3,776,574 A | 12/1973 | Henderson et al. |
| 4,981,353 A | 1/1991 | Murakawa et al. |
| 6,317,387 B1 | * 11/2001 | D'Amaddio et al. ........ 367/129 |

FOREIGN PATENT DOCUMENTS

JP    8136240    5/1996

* cited by examiner

Primary Examiner—Stephen Avila
(74) Attorney, Agent, or Firm—Klarquist Sparkman, LLP

(57) ABSTRACT

The present invention relates to an inspection system for inspection of an object, comprising at least an image recording means carried by an inspector, a display unit, a storage unit and a contact free positioning unit. The storage unit is arranged to store at least an image taken by said imaged recording unit in relation to a position given by said positioning unit and/or a time index.

18 Claims, 5 Drawing Sheets

METHOD AND ARRANGEMENT RELATING TO INSPECTION

CROSS-REFERENCE TO RELATED APPLICATION

Figure 1:
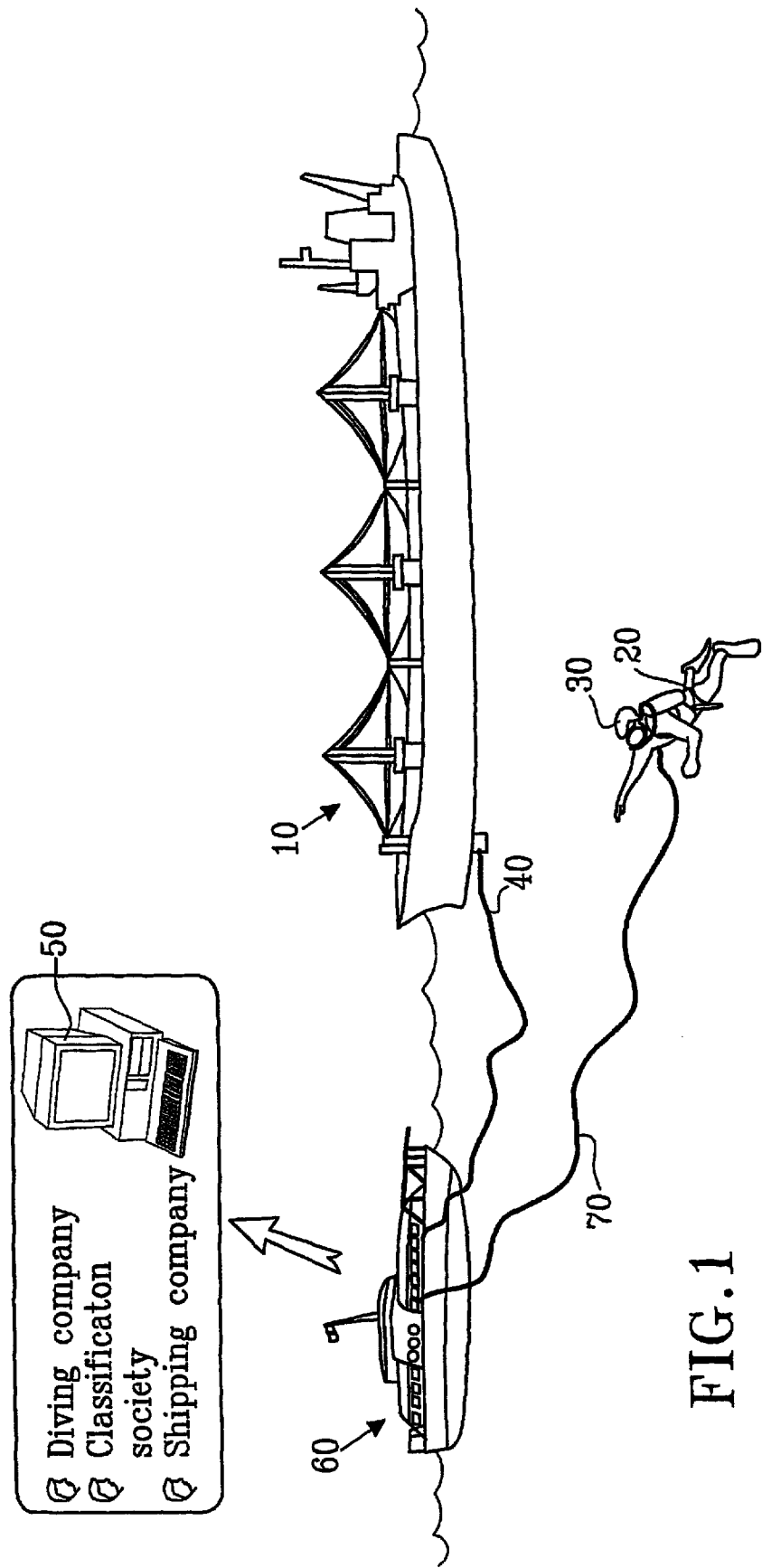

This is a continuation of International Application No. PCT/SE01/01182, filed May 25, 2001, which claims priority from both Swedish Application No. 0001970-3, filed May 24, 2000, and U.S. Provisional Application No. 60/207,133, filed May 24, 2000.

TECHNICAL AREA

The present invention relates to an inspection system for inspection of an object, at least comprising an image recording unit supported by an inspector, a display unit and a storage unit. The invention particularly relates to inspection of ships or the like.

THE STATE OF THE ART

Ships are to be inspected at close intervals according to law. The inspection shall occur in a dock or by divers filming the complete bottom of the ship.

At conventional diving inspections, the inspection often occur at sea since the visibility is much better there than at the harbours. The person to perform the inspection goes out to the ship in a separate boat, wherein all the equipment is brought. At a diving inspection, except for three persons of the diving company, representatives of the classification society and the shipping company are present as well.

During the inspection, the diving company also has divers in the water being equipped with a camera and sound transmission and a person supervising the diver. The third person of the diving company is situated in front of a TV screen, together with the representatives of the classification society and the shipping company. The pictures of the camera of the divers are shown on the TV-screen, this picture is stored on videotape as well. The persons in front of the TV-screen deciding which action to be performed on the ship. At this time, notes concerning the damages and the counting mechanism of the video are made.

The diver swims from starboard to port and then moves approximately 2 m towards the prow and then swims from port to starboard. This pattern is repeated.

The diver keeps track of his position with respect to the ship by reading a measuring tape, which has been placed in the middle under the ship before the diver starts the inspection. The diver relays his position to the person watching on the TV-screen.

A ship inspection consists of diving work and writing reports for the diving company. The diving work itself takes approx. 8–12 hours for a ship of average-size. After the diving work is completed writing reports remains. It takes approx. 8 hours to process the videotapes and select frames of the film based on the remarks and writing text to each respective remark.

In U.S. Pat. No. 3,776,574 an inspection system for hulls of vessel is described, wherein a diver swims backwards and forwards under the ship and films the hull of the vessel. For orientation and positioning, the hull of the vessel is marked by painting squares and by numbering. At the inspection the areas and their identity numbers are filmed and recorded. According the description above, this system is time-consuming by the marking procedure, the storing and the recovering of information. Criticised areas must be searched and/or registered for manual scanning later on.

SHORT DESCRIPTION OF THE INVENTION

The object of the present invention is to provide a system simplifying the inspection work and reduce the inspection and the reporting time and facilitating the documentation and the search in the documentation.

In a system, according to the invention, the position of the diver is corresponded to the film and this is displayed on e.g. a computer monitor.

Additional advantages of the system are:

Ensured inspection results, improved control of the position of the diver, easier to find specific check points, e.g. valves, etc.

the documentation of where the diver has been, easy to study specific parts of the ship afterwards by clicking on a drawing, less documentation work production of different reports directly from a computer, appropriate for several applications, e.g. harbour inspections and inspections within offshore, and inspections of larger objects on shore, and the system is built in such a way that it is possible to exchange to diver to a ROV (unmanned submarine robot). ROV is gaining land within the diving business.

These objects have been solved by the system initially described comprise a contact free positioning unit and that the storage unit is arranged to at least store a image taken of said image recording unit in relation to a position given by said positioning unit and/or a time index. The system can comprise means for connecting a time and/or position index to said position and image and a note. Moreover, the system can comprise means for digitally storing images and performing search for an event by means a time- and/or position- and/or event index.

In one embodiment, the positioning unit comprises: a transmitter/receiver located on a known position adjacent the object to be inspected, a receiver/transmitter located on the inspector, whereby the transmitter/the receiver sends out a coded sound signal and the receiver/the transmitter responds with a coded signal, which is received by the transmitter/the receiver and the position of the receiver/the transmitter is decided with assistance of time and direction. Other positioning systems are known from e.g. U.S. Pat. No. 4,981,353 and JP 81-36240.

In another embodiment, the positioning unit comprises: a number of probes located on known positions, a transmitter located on the inspector, whereby the transmitter sends out a sound signal and the probes receive the signals and decides the position of the transmitter with assistance of a time difference between the probes and that the known positions are received either by placing the probes on the object or connecting the probes to a positioning system and connecting the object to the positioning system.

In yet another embodiment, the positioning unit comprises: a digital compass module containing of a number of magnetic axes and tilting sensors as well, compensating for the inclination of the magnetic axes and that the compass module keeping track on its position.

In an alternative embodiment, the positioning unit comprises: an inertia gyro sensing the direction and speed and keeping track of the position by counting from a given start position.

Preferably, said inspector is a diver or a robot.

The system also includes a database arranged to store the incoming data, comprising a model of the ship, the image taken by the image recording unit, a position of the positioning system, sound of a sound recording unit and remarks provided with time index as well. The input signals of the database comprises amongst others: one or several drawings of the object, which are re-processed to a model of the ship, a sound signal of one or several channels being converted to a standard format and provided with time index, video signal being converted to a standard format and provided with a time index and is eventually compressed, position being converted to a relative position and is provided with a time index, and remarks, which via a user interface is introduced, is provided with time index and stored.

The invention also refers to a method at inspection of an object by means of a system comprising at least an image recording means carried by an inspector, a display unit and a storing unit. The method comprising providing a contact free positioning unit and a device of the storing unit for at least storing an image recorded of said image recording unit in relation to a position given of said positioning unit and/or a time index.

Moreover, the method comprises the step to connecting a time- and/or position index with said position and image and a note.

Particularly, the invention relates to a method at an inspection of a floating object in a medium, particularly a ship, by means of a system comprising at least an image recording unit carried by an inspector, a computer unit communicating with a storage unit. The method comprises providing a contact free positioning unit at least at the object, and an arrangement of the storage unit for at least storing an image taken of said image recording unit in relation to a position given of said positioning unit and/or a time index. The inspection starts with a digital drawing of the object is stored in the computer or a storage unit. The image recording unit and a signal of the positioning unit is connected to the computer. The position of the inspector is shown as a dot on the computer stored drawing. According to a preferred embodiment, the position of the inspector is shown together with an image of the image recording unit is shown substantially continuously while the inspector moves from one position to a second position. In one embodiment continuous registration of the position of the inspector is carried out. Preferably, at the appearance of a remark being stored and connected with an image, captions and at least a part of the drawing is connected with the position of the drawing. At the study of the inspection data including notes is recovered by pointing at a drawing corresponding said drawing by means of an indicator in a registered movement pattern of the inspector.

SHORT DESCRIPTION OF THE DRAWINGS

Figure 2:
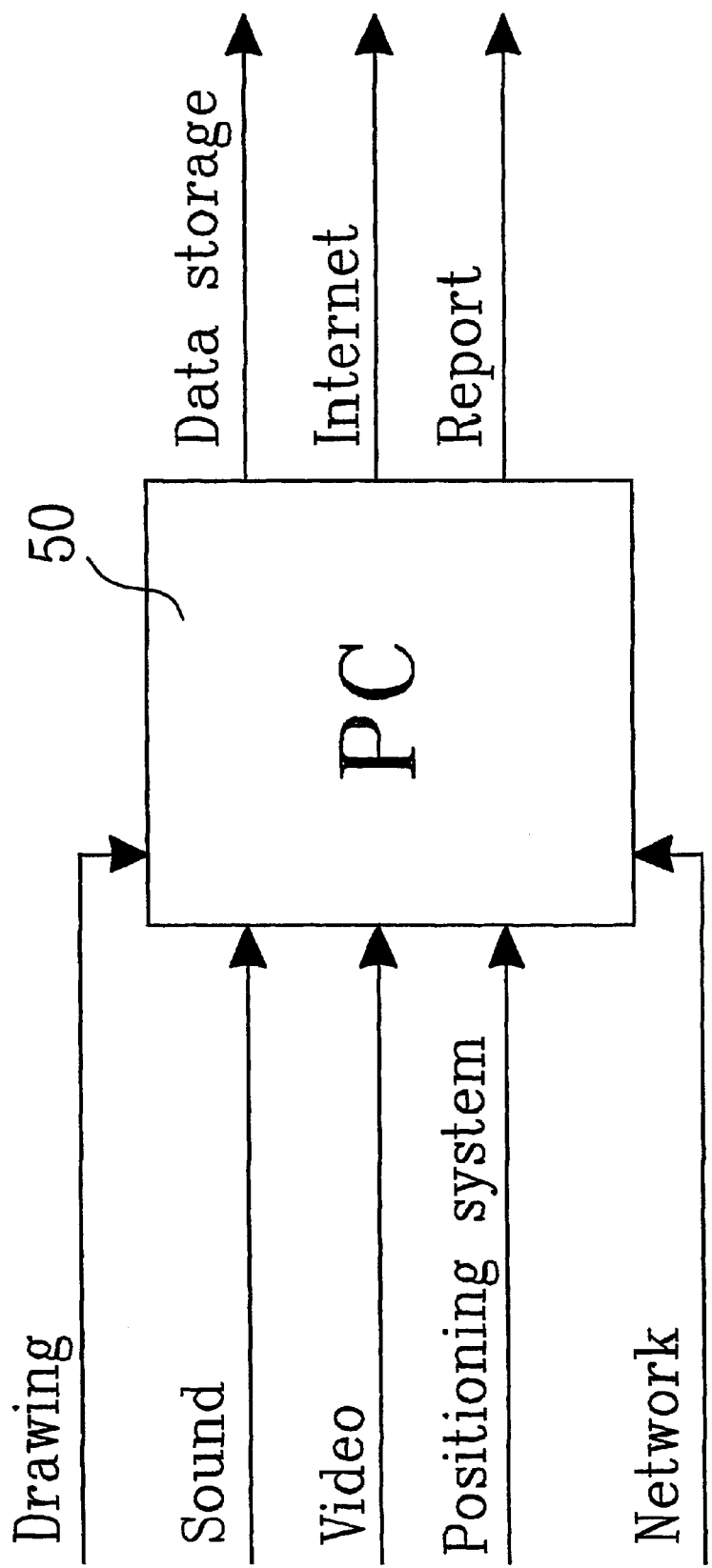
Figure 3:
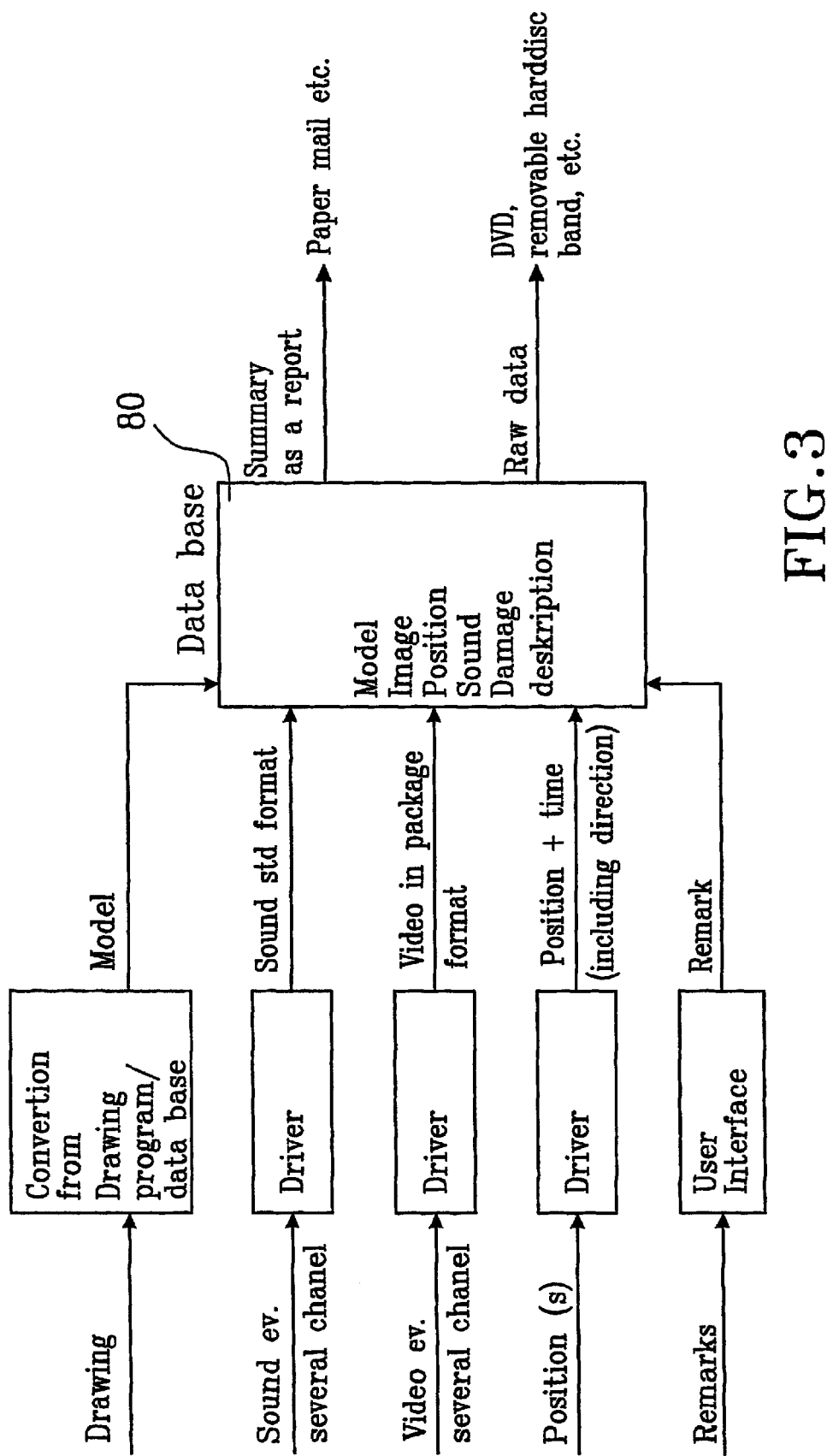
Figure 4:
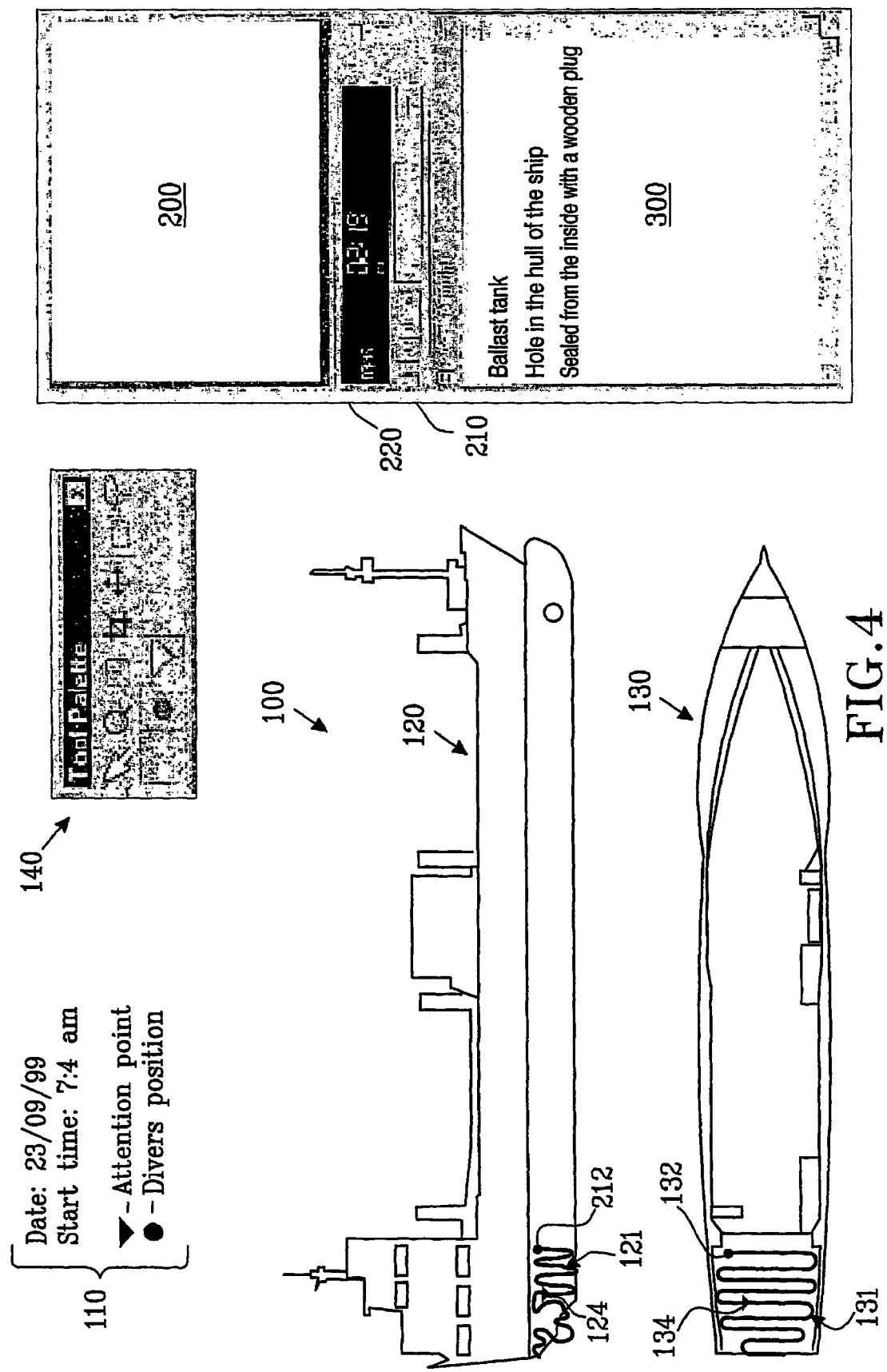
Figure 5:
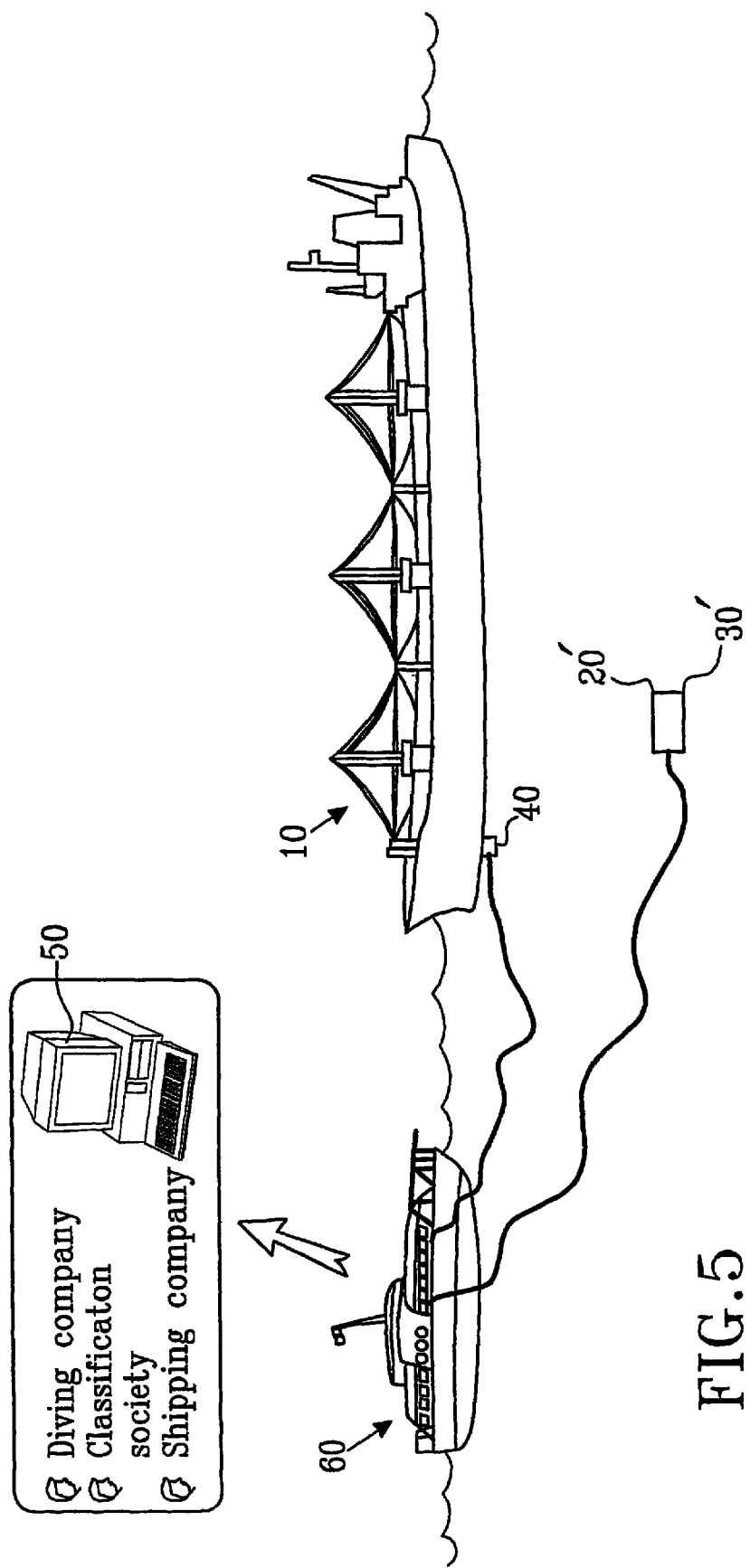

In the following, the invention will be described with reference to the embodiment shown at enclosed drawings, in which:

FIG. 1 schematically shows a first embodiment of a system according to the present invention, FIG. 2 shows a comprehensive block diagram of the system according to the invention, FIG. 3 shows a comprehensive block diagram of the storage part in the computer system according to the invention, FIG. 4 shows a screen layout in the system according to the invention, and FIG. 5 schematically shows a second embodiment of a system according to the present invention.

DESCRIPTION OF THE EMBODIMENTS

In the following, a described embodiment relates to a system being used at the inspection of ships. However, the invention can be used at the inspection and scrutinize work of different objects.

A system for inspection of e.g. a ship 10 (or another floating object or immersed in a volume) according to the invention shown in FIG. 1 substantially comprises a diver 20 provided with a sound and image recording unit 30, a positioning unit 40 and a computer unit 50 as well.

The diver 20 carries conventional diving equipment provided with a communication means and a camera 30 arranged on e.g. the helmet for recording images and sound, for facilitating the inspection work.

The camera 30 can be a conventional submarine camera supplying analogous and or digital images and sound as well. However, the sound recording can be carried out by means of separate equipment. The communication between the diver and the inspection ship 60 can be performed via cables 70 and/or wireless via radio.

The positioning unit can consist of any positioning system. Preferably, one or several of the following systems can be used. However, other equipment appropriate for the invention can also be present.

The positioning system can comprise:

Ultra short baseline (USBL): a transmitter/receiver is placed on a known position. A transfer is placed on the diver or the ROV. The transmitter/receiver sends a coded sound signal. The transponder responds with a coded signal. The transmitter/receiver receives the signal and decides the position of the transponder with assistance of the time and direction.

Long Base Line (LBL): a number of probes are placed on known positions. A transmitter is located on the diver or the ROV. The transmitter sends a sound signal, the four probes receive the signal and decide the position of the transmitter with assistance from the time difference between the probes. The known positions are received either by placing the probes against e.g. the ship or connecting these with the GPS system and connecting the ship with the GPS system.

Digital Compass module: the system comprises a digital compass module containing three magnetic axes and two tilting sensors. The tilting sensors compensates for the inclination of the magnetic axes. The compass module keeping track of its position. A digital compass module can be used e.g. on a ROV if it is completed with a speedometer. By the fact that the direction and the speed of the ship is known, the position can be calculated. The module must be provided with a start position. However, a magnetic compass module is not considered as appropriate when e.g. a ship can interfere the magnetic field.

Inertia gyro: being used in several military applications. The gyros sense the direction and the speed, and keeping track of the position by calculating from a given start position.

FIG. 2 shows a block schema of the computer unit 50. A video (camera) and sound recording unit, signal of the positioning system, drawing basis from a drawing data base and eventually another communications means, e.g. for communication in a network, are directly or indirectly connected to the computer unit. Data processed in the data unit is transferred as a report, to a storage unit or over a network, e.g. an intranet or the Internet. The system also gives an opportunity for performing the inspection at a distance, i.e. representatives of the diving company, the classification society or the shipping company do not need to be present on the accompanying boat, but can follow the inspection via the Web.

The database 80, being schematically shown in FIG. 3, is arranged to store the incoming data, preferably processed data. In the database a model of the ship is stored, the film recorded by the camera of the diver, the position of the positioning system, the sound of the sound recording unit and remarks are provided with time index before they are stored. Consequently, the input signals of the database comprise:

one or several drawings over the ship, which are re-processed to a model of the ship, sound from one or several channels, which are converted to a standard format and provided with time- and/or position index by means of e.g. a driving routine, video signal of one or several channels being converted to a standard format and provided with time- and/or position index, and are eventually compressed, by means of e.g. a driving routine position being converted to a relative position and provided with time- and/or position index by means of e.g. a driving routine, and remarks, e.g. compensation remarks, being introduced via a users interface and provided with time/or position index and is stored.

A report can be put together from the database and data can be stored in an external medium, preferably in digital form, such as DVD, a detachable hard disc, DAT or the like.

FIG. 4 shows a shield layout at the inspection. The lay-out comprises a number of fields:

in a main field 100 a drawing of the ship is shown, both a side-view and a view from a above (other views are also possible), in a second field 200 the images of the camera are shown, and in a third field 300 the remarks are shown in form of text.

By the fact that a digital storing is used the damages can be connected with the images and a quick search and processing are provided.

In the main field 100 further information is present. In a lower field 110, key to the signs are shown concerning the ship being inspected and time/date for the start of the inspection as well.

The model of the ship 120 and 130, being shown in the main field, is provided with a trace 121/131 showing the path of the diver and a dot 122/132 showing the position of the diver. By using two views, a "three-dimensional" position is obtained with respect to the ship. The main field may also comprise a toolbar 140 for zooming-in, displacement of views, copying, etc.

Except for the viewing screen, the image and video field 200 also comprise means 210 for controlling the image, such as playback, storing, winding and the like. The time is also stated in a field 220.

The remark field 300 is really a notepad wherein it is possible to introduce information, e.g. via the keyboard, which is connected together with the shown image and the position of the diver via time index.

The function of the system is described in the following not limited example: The inspection work starts with a digital drawing of the ship 10 being stored in the computer 50 (new ships have digital drawings, the drawings are scanned for older ships). The computer replaces the TV-screen being used at a conventional inspection.

The video camera 30 and a signal of the positioning system 40 are connected to the computer. The position of the diver is shown as a dot on the drawing being data stored.

The people following the inspection from the accompanying ship 60 see the position of the diver together with the video film (field 200, FIG. 4) while the diver swims from one side to the other side. They have the ability to verify any place where the diver films, making it easier to help the diver find particular locations on the ship and to verify that the diver has been everywhere.

A still picture is stored and connected with all remarks, captions and a drawing having the position of the damage. This information can be immediately printed after the inspection has concluded. The total work is stored on a storing media, such as a DVD disc. Consequently, report writing is greatly simplified.

To study the inspection data, one only needs to click, by means of a mouse or the like, on the part of line 124/134 representing the position for which data is desired. This is preferable to the prior art system which requires reviewing the video until the correct position on the ship is found. The video for a single inspection is approximately eight hours.

Off course, the diver can be replaced with a robot 20' a so-called ROV containing an image-/sound recording unit 30' such as illustrated in FIG. 5. In this case, a means is arranged for controlling the robot from the inspection ship.

While we have illustrated and described preferred embodiments of the invention, it is realized that several variations and modifications are possible within the scope of the accompanying patent claims.

What is claimed is:

1. An inspection system for inspection of an object comprising:

at least one image recording means carried by an inspector;

a display unit;

a storage unit; and a contact free positioning unit;

the storage unit being arranged to store at least an image taken by said image recording unit in relation to a position given by said positioning unit and/or a time index, said system further including means for storing images digitally and performing a search for an event by means of a time, position and/or event index, said system further including means for connecting a time and/or a position index with said position and image and a note.

2. The system of claim 1 wherein said positioning unit includes a transmitter/receiver placed on a known position adjacent the object to be inspected, and a receiver/transmitter placed on the inspector, whereby the transmitter/receiver sends a coded sound signal and the receiver/transmitter responds with a coded signal, which is received by the transmitter/receiver and the position of the receiver/transmitter is decided with assistance of time and direction.

3. The system of claim 1 wherein said inspector is a diver.

4. The system of claim 1 wherein said inspector is a robot.

5. The system of claim 1 further comprising a database arranged to store incoming data including a model of the ship, the image recorded by the image recording unit, a position of the positioning system, sound from a sound recording unit and remarks provided with time index.

6. An inspection system for inspection of an object comprising:

at least one image recording means carried by an inspector;

a display unit;

a storage unit; and a contact free positioning unit;

the storage unit being arranged to store at least an image taken by said image recording unit in relation to a position given by said positioning unit and/or a time index, said system further including means for storing images digitally and performing a search for an event by means of a time, position and/or event index, the positioning unit including an inertia gyro, sensing the direction and speed, and keeping track of the position by calculating from a given start position.

7. An inspection system for inspection of an object comprising:

at least one image recording means carried by an inspector;

a display unit;

a storage unit; and a contact free positioning unit;

the storage unit being arranged to store at least an image taken by said image recording unit in relation to a position given by said positioning unit and/or a time index, said system further including means for storing images digitally and performing a search for an event by means of a time, position and/or event index, the positioning unit including a number of probes placed on known positions, a transmitter placed on the inspector, whereby the transmitter sends a sound signal, and the probes receive the signal and decide the position of the transmitter with assistance from a time difference between the probes, and the known positions are received either by placing the probes against the object or connecting these to a positioning system and connecting the object to the positioning system.

8. An inspection system for inspection of an object comprising:

at least one image recording means carried by an inspector;

a display unit;

a storage unit; and a contact free positioning unit;

the storage unit being arranged to store at least an image taken by said image recording unit in relation to a position given by said positioning unit and/or a time index, said system further including means for storing images digitally and performing a search for an event by means of a time, position and/or event index, the positioning unit including a digital compass module containing a number of magnetic axes and tilting sensors to compensate for the inclination of the magnetic axes and allow the compass module to keep track of its position.

9. A method of inspecting a floating object in a medium, particularly a ship, using a system having at least one image recording means carried by an inspector and a computer unit communicating with a storage unit, the method comprising:

providing a contact free positioning unit at least at the object;

arranging the storage unit for at least digitally storing an image taken by said image recording means in relation to a given position of said positioning unit and/or a time index;

performing a search for an event by means of a time, position and/or event index; and at the appearance of a remark, storing an image and connecting the image to captions such that at least a part of the drawing is connected with the position of the drawing.

10. An inspection system for inspection of an object comprising:

at least one image recording means carried by an inspector;

a display unit;

a storage unit; and a contact free positioning unit;

the storage unit being arranged to store at least an image taken by said image recording unit in relation to a position given by said positioning unit and/or a time index, said system further including means for storing images digitally and performing a search for an event by means of a time, position and/or event index, the system including database being arranged to store incoming data including a model of the ship, the image recorded by the image recording unit, a position of the positioning system, sound from a sound recording unit and remarks provided with time index, wherein input signals of the database include one or several drawings over the ship, which are re-processed to a model of the ship, sound of one or several channels, which are converted to a standard format and provided with a time index, video signal being converted to a standard format and provided with time-index and are eventually compressed, position being converted to a relative position provided with a time index, and remarks which are brought in via a user interface, provided with time index and stored.

11. A method of inspecting an object using a system having at least one image recording means supported by an inspector, a display unit and a storing unit, the method comprising:

providing a contact free positioning unit;

arranging the storing unit for storing at least one image taken by said image recording means in relation to a given position by said positioning unit and/or time index; and connecting a time and/or position index with said position and image and a note.

12. A method of inspecting a floating object in a medium, particularly a ship, using a system having at least one image recording means carried by an inspector and a computer unit communicating with a storage unit, the method comprising:

providing a contact free positioning unit at least at the object;

arranging the storage unit for at least digitally storing an image taken by said image recording means in relation to a given position of said positioning unit and/or a time index;

performing a search for an event by means of a time, position and/or event index; and recovering inspection data including notes by pointing at a drawing corresponding said drawing by means of an indicator in a registered movement pattern of the inspector.

13. A method of inspecting a floating object in a medium, particularly a ship, using a system having an image recording means supported by an inspector and a computer unit communicating with a storage unit, the method comprising:

providing a contact free positioning unit near the object;

arranging the storage unit for at least digitally storing an image taken by said image recording means in relation to a given position of said positioning unit and/or a time index; and performing a search for an event by means of a time, position and/or event index.

14. The method of claim 13 wherein the inspection starts with a digital drawing of the object that is stored in the computer or storage unit.

15. The method of claim 13 including connecting the image recording means and a signal of the positioning unit to the computer unit.

16. The method of claim 13 or 14 including showing the position of the inspector as a dot on the computer stored drawing.

17. The method of claim 13 or 14 including showing the position of the inspector with an image of the image recording unit substantially continuously while the inspector moves from a position to a second position.

18. The method of claim 17 including performing continuous registration of the position of the inspector.

* * * * *